May 3, 1966 E. S. BOERNER Plant Pat. 2,628
ROSE PLANT
Filed Jan. 14, 1965
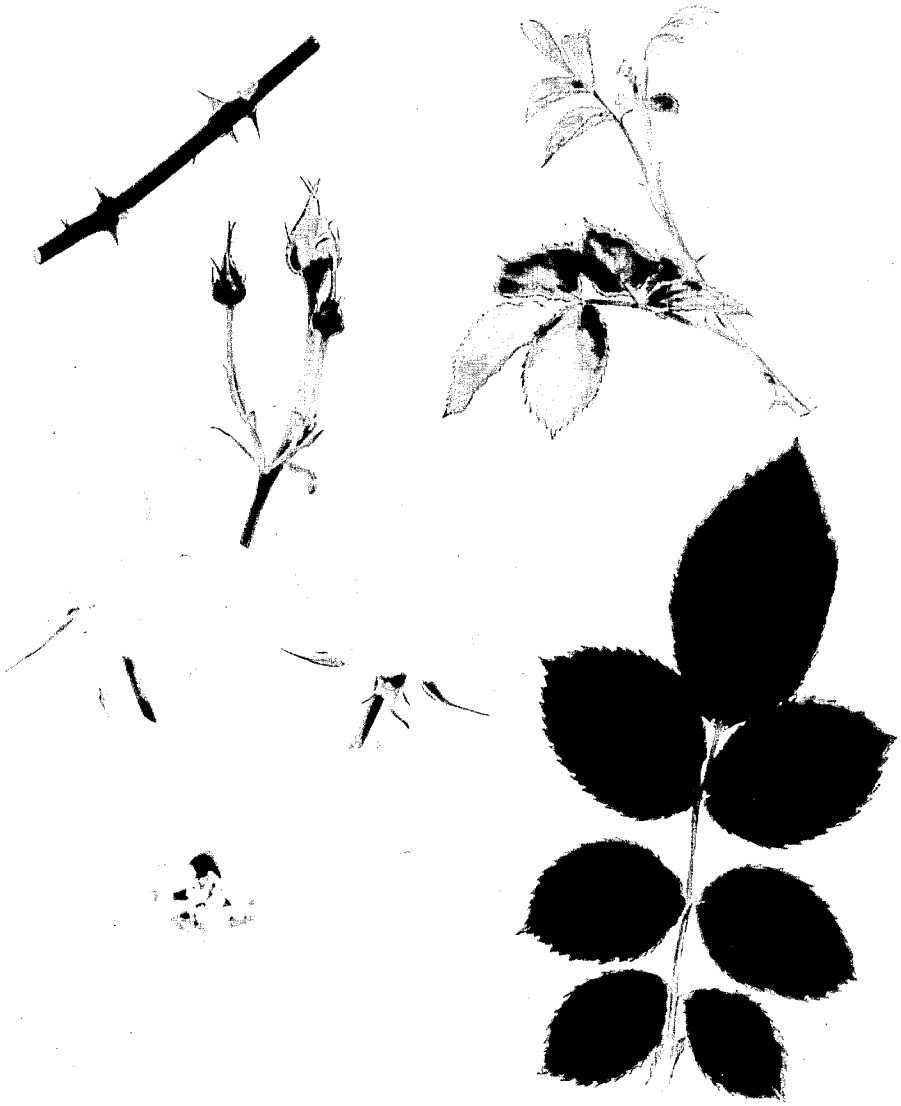
Inventor.
E. S. Boerner
By: Robb & Robb
Attorneys.

United States Patent Office

Plant Pat. 2,628
Patented May 3, 1966

2,628
ROSE PLANT

Eugene S. Boerner, Newark, N.Y., assignor to Jackson & Perkins Company, Newark, N.Y., a corporation of New York Filed Jan. 14, 1965, Ser. No. 425,650
1 Claim. (Cl. Plt.—25)

The present invention relates to a new and distinct variety of rose plant of the floribunda class, which was originated by me by crossing an unnamed and unpatented yellow-flowered seedling of "Pinocchio" (Plant Patent No. 484) with the variety "Spartan" (Plant Patent No. 1,357).

The primary objective of this breeding was to produce a new rose variety bearing smaller floribunda clustered type flowers. This objective was achieved, along with other desirable improvements, as evidenced by the following unique combination of characteristics which are outstanding in the new variety and which distinguish it from its parents, as well as from all other varieties of which I am aware:

(1) Good foliage retaining qualities;

(2) Good flower petalage and good strength of the petals;

(3) A distinctive and attractive general color tonality of the flowers corresponding to Coral Red, overcast with Peach Red, which is an unusual coloration in a cluster type of floribunda rose; and (4) Good color retaining qualities of the flowers.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.

*Seed parent.*—An unnamed yellow-flowered seedling of "Pinocchio."

*Pollen parent.*—"Spartan."

Classification:

*Botanic.*—Floribunda.

*Commercial.*—Floribuna.

*Flower*

(Observations made from specimens grown outdoors at Newark, New York, in the early morning during the early part of the month of September.)

Blooming habit: Recurrent—continuous.

Bud:

*Size.*—Medium.

*Form.*—Ovoid; not affected by wet or hot weather.

*Color.*—When sepals first divide—Nopal Red, Plate 1. When petals begin to unfurl—Scarlet-Red, Plate 1. When half-blown: Inside of petals—Scarlet, Plate 1, very lightly overcast with Grenadine Red, Plate 2; reverse of petals—Scarlet-Red, Plate 1, overcast with Scarlet, Plate 1.

*Sepals.*—Slightly branched; curl back when petals begin to unfurl. Color: Inside—Chrysolite Green, Plate 31; outside—Light Bice Green, Plate 31.

*Calyx.*—Color—Lettuce Green, Plate 5. Shape—pear. Size—small. Aspect—smooth. Odor when rubbed—none.

*Peduncle.*—Length—medium. Aspect—smooth. Strength—erect; slender. Color—Lettuce Green, Plate 5.

*Opening.*—Opens up well; is not affected by adverse weather conditions.

Bloom:

*Size.*—Medium. Average size when fully expanded—from 2½ inches to 3 inches.

*Borne.*—Several together and in rounded clusters.

*Stems.*—Medium length; strong.

*Form (when first open).*—Cupped. Permanence—retains its form to the end but outer petals curl back.

*Petalage.*—Double (full but open center). Number of petals under normal conditions—50.

*Color.*—Center of flower—Coral Red, Plate 13, lightly overcast with Peach Red, Plate 1. Outer petals—Light Coral Red, Plate 13, very lightly overcast with Peach Red, Plate 1. Base of petals (aiglet)—Empire Yellow, Plate 4. Inside of petals—Coral Red, Plate 13, overcast with Peach Red, Plate 1. Reverse of petals—Peach Red, Plate 1. General tonality from a distance—Coral Red, Plate 1, overcast with Peach Red, Plate 1.

*Discoloration.*—General tonality at end of first day—Coral Red, Plate 13. Second day—Coral Red, Plate 13, lightly overcast with Peach Red, Plate 1. Third day—Coral Red, Plate 13, overcast with Peach Red, Plate 1.

Petals:

*Texture.*—Leathery; is not affected by wet or hot weather.

*Appearance.*—Inside—satiny. Outside—shiny.

*Form.*—Oval.

*Arrangement.*—Imbricated (regularly arranged shingle-like).

*Petaloids in center.*—Few; small.

*Persistence.*—Drop off cleanly.

*Fragrance.*—Moderate. Nature—tea (average hybrid tea scent).

*Lasting quality.*—On the plant—long. As cut flower—long.

*Genital organs*

Stamens, anthers: Small; many; regularly arranged around styles. Color—Buff Yellow, Plate 4.

Stamens, filaments (threads): Medium length. Color—Citron Yellow, Plate 16.

Pollen: Color—Maize Yellow, Plate 4.

Styles: Bunched; uneven length; medium length; thin.

Stigmas: Color—Chalcedony Yellow, Plate 17.

Ovaries: All enclosed in calyx.

Hips: None.

Seeds: None.

*Plant*

Form: Bush.

Growth: Vigorous; compact; upright.

Foliage: Compound of 5 to 7 leaflets.

*Size.*—Medium.

*Quantity.*—Normal.

*Color.*—New foliage: Upper side—Lettuce Green, Plate 5, with Serrations Nopal Red, Plate 1; under side—Cosse Green, Plate 5. Old foliage: Upper side—Varley's Green, Plate 18; under side—Light Elm Green, Plate 17.

*Shape.*—Oval pointed.

*Textured.*—Upper side—glossy. Under side—smooth.

*Ribs and veins.*—Ordinary.

*Edge.*—Serrated (saw toothed).

*Serration.*—Both double and single; small.

*Leaf stem.*—Color—Rainette Green, Plate 31. Under side—smooth.

*Stipules.*—Short; smooth.

Wood:

*New wood.*—Color—Lettuce Green, Plate 5. Bark—smooth.

*Old wood.*—Color—Cress Green, Plate 31. Bark—smooth.

Thorns:

*Thorns.*—Quantity: on main stalks from base—ordinary; on laterals from stalk—ordinary. Form—narrow base; medium length; straight and some hooked downward. Color (when young)—Light Vinaceous Cinnamon, Plate 29. Position—irregular.

*Prickles.*—Quantity: On main stalks—none; on laterals—none.

*Short needles.*—Quantity: On main stalks—none; on laterals—none.

I claim:

A new and distinct variety of rose plant of the floribunda class, substantially as herein shown and described, characterized particularly as to novelty by the unique combination of good foliage retaining qualities, good flower petalage and good strength of the petals, a distinctive and attractive general color tonality of the flowers corresponding to Coral Red, overcast with Peach Red, which is an unusual coloration in a cluster type of floribunda rose, and good color retaining qualities of the flowers.

No references cited.

ANTONIO F. GUIDA, *Acting Primary Examiner.*